United States Patent [19]

Orentreich

[11] Patent Number: 4,496,556
[45] Date of Patent: Jan. 29, 1985

[54] TOPICAL APPLICATIONS FOR PREVENTING DRY SKIN

[76] Inventor: Norman Orentreich, 140 E. 72nd St., New York, N.Y. 10021

[21] Appl. No.: 408,548

[22] Filed: Aug. 16, 1982

[51] Int. Cl.³ .............................................. A61K 31/56
[52] U.S. Cl. ...................................................... 514/178
[58] Field of Search ................................. 424/243, 59

[56] References Cited

U.S. PATENT DOCUMENTS 3,162,631 12/1964 Pike ................................. 260/239.57
4,005,200 1/1977 Utsumi et al. .

OTHER PUBLICATIONS

Chemical Abstracts, (1969), vol. 70, Par. 34,776t, An Abstract of a Publication by Pochi et al., "J. Invest. Dermatol.", 1969, 52(1), 32–36.
Chemical Abstracts, (1970), vol. 72, Par. 118,214n, An Abstract of a Publication by Oertel et al., "Hoppe-Seyler's Z. Physiol. Chem.", 1970, 351(3), 84–86, (Germ).
"The Effect of Aging on the Activity of the Sebaceous Gland in Man", by Pochi, P. E. and Strauss, J. S., *Advances in Biology of Skin*, vol. VI: Aging, edited by Montagna, W., Pergamon Press, N.Y., (1965).
"Biological Activity of Dehydroepiandrosterone Sulfate in Man", by Drucker, W. D., Blumberg, A. M., Gandy, H. M., David, R. R. and Verde, A. L., *Journal of Clinical Endocrinology and Metabolism*, 35: 48–54, (1972).
"Antiobesity Drug may Counter Cancer, Aging", *Science News*, Jan. 17, 1982.
"Amazing New Drug that may Lead to Longer Life", Kotulak, R., *Chicago Tribune*, Jan. 22, 1981.

*Primary Examiner*—Elbert L. Roberts
*Attorney, Agent, or Firm*—Panitch, Schwarze, Jacobs & Nadel

[57] ABSTRACT

The severity in incidence of menopausal or age related skin dryness in particular localized areas of the body can be reduced or eradicated by topical administration of effective dosages of the free alcohol form of dehydroepiandrosterone or its derivatives.

6 Claims, 5 Drawing Figures

TOPICAL APPLICATIONS FOR PREVENTING DRY SKIN

CROSS REFERENCE TO RELATED APPLICATION

This application is related to my copending patent application Ser. No. 345,835, filed Feb. 4, 1982, now abandoned.

FIELD OF THE INVENTION

The present invention relates to a method to prevent and/or treat dry skin and loss of natural oiliness by the external application of effective dosages of the free alcohol of dehydroepiandrosterone or its derivatives, for example, acetate, in suitable vehicles.

BACKGROUND OF THE INVENTION

Almost all menopausal and post-menopausal women, many women over thirty-five, and most women over forty years of age, and some older men frequently complain that the natural oiliness of their skin is markedly diminished.

A paper entitled "The Effect of Aging on the Activity of the Sebaceous Gland in Man" by Pochi. P. E. and Strauss, J. S. that was published in *Advances in Biology of Skin,* Vol VI: Aging, edited by Montagna, W., Pergamon Press, N.Y. (1965), described the reduction in mean sebum (oil) secretion in males and females in relation to advancing age. FIG. 1 herein illustrates this reduction in mean sebum production with aging.

Testosterone therapy increases skin oil production in menopausal and post-menopausal women. However, it produces unwanted superfluous facial and body hair and other systemic masculinizing side effects and is therefore rarely used.

Dehydroepiandrosterone is a steroid. It and its sulfate are secreted by the adrenal glands, circulate in the bloodstream, and are excreted in urine as derivatives of dehydroepiandrosterone.

As shown in FIG. 2, dehydroepiandrosterone sulfate levels in the blood have been shown to reach a peak in early adult life and then gradually decline with advancing age (Orentreich Foundation for the Advancement of Science, Inc., Annual Report, 1979).

The structure for dehydropiandrosterone is as follows:

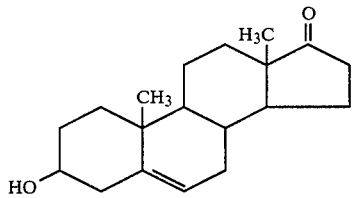

In a study entitled "Biological Activity of Dehydroepiandrosterone Sulfate in Man" by Drucker, W. D., Blumberg, A. M., Gandy, H. M., David, R. R., and Verde, A. L., that was published in the *Journal of Clinical Endocrinology and Metabolism,* 35: 48-54 (1972), sebum production was used as a measure of androgenic activity associated with the oral administration of dehydroepiandrosterone sulfate. Drucker et al., however, did not address the problem of dry skin in normal older women and some older men. Indeed, the experiments of Drucker et al. were conducted with five abnormal, androgen-deficient, hypogonadal males, ages 15, 20, 30, 34 and 35, and a three-month-old female with 21-trisomy syndrome.

In U.S. Pat. No. 4,005,200, a new use of dehydroepiandrosterone sulfate as a parturient canal conditioning agent was disclosed. U.S. Pat. No. 4,005,200 describes systemic administration of dehydroepiandrosterone sulfate to a pregnant female during the 37th to 39th week of pregnancy to improve the maturity of the parturient canal and the sensibility of the uterine musculature to oxytocin. U.S. Pat. No. 4,005,200 mentions that it had been proposed to use dehydropiandrosterone sulfate clinically in combination with estrogens in the treatment of various syndromes associated with climacterium, but the problem of skin dryness was not addressed in this patent.

In recent articles (Jan. 17, 1982 edition of *Science News,* "Antiobesity Drug May Counter Cancer, Aging"; Jan. 22, 1981 edition of the *Chicago Tribune,* "Amazing New Drug That May Lead to Longer Life", Kotulak, R.), uses of dehydroepiandrosterone and analogs thereof were described to counter obesity and prevent cancer. These articles did not, however, address the problem of skin dryness.

I previously discovered a method (described in my prior copending application Ser. No. 345,835 now abandoned) for treating dry skin in humans by internally administering an effective dosage of the alcohol and/or one or more salts of dehydroepiandrosterone. This treatment is particularly useful in treating dry skin in menopausal women. This treatment can also be employed to treat premenopausal females with a low endogenous dehydroepiandrosterone production. Furthermore, males who suffer from dry skin due to low plasma levels of testosterone and/or dehydroepiandrosterone and its sulfate can be treated in accordance with my previous invention.

Menopausal and post-menopausal and other older women usually have a distinct reduction in dehydroepiandrosterone sulfate levels in the blood which is generally accompanied by a reduction in the oil production of the skin and results in dryness of the skin. Such dry skin problems generally affect the entire body. The face and head, however, have the highest population of sebaceous glands and therefore those areas are the mose vulnerable to these problems. I previously found that the internal administration of the alcohol or one or more salts of dehydroepiandrosterone increases the blood level of dehydroepiandrosterone and its sulfate and reduces skin dryness. The reduction of activity of sebaceous glands with aging and at the onset of menopause is reversed by the internal administration of dehydroepiandrosterone alcohol or dehydroepiandrosterone sulfate.

Xeroderma, i.e., dry skin, can be caused by a multiplicity of factors and can be aided by the use of exogenous and water retentive products. I previously found that internal administration of dehydroepiandrosterone alcohol or dehydroepiandrosterone sulfate increases the endogenous production and secretion of natural sebum and enhances the water protective barrier of the skin, thus acting as a natural moisturizer.

Oral ingestion or other systemic administration of dehydroepiandrosterone or its derivatives results in an increase in oil production by all sebaceous glands over the entire body, an effect that is frequently undesirable or unnecessary. The present invention permits obtaining the above-described desirable effects on a localized basis, only at the places where such effects are desired or necessary.

SUMMARY OF THE INVENTION

There has now been discovered a method of treating dry skin in a patient which involves topically administering to the area of dry skin on the patient an effective amount of dehydroepiandrosterone and/or a pharmaceutically acceptable, therapeutically effective derivative thereof. One such derivative of dehydroepiandrosterone is the acetate derivative. Other non-limiting derivatives which may be utilized in this invention include valerate, enanthate, and fatty acid ester derivatives.

BRIEF DESCRIPTION OF THE DRAWINGS

For the purpose of illustrating the invention, there is provided in the drawing a form which is presently preferred; it being understood, however, that this invention is not limited to the precise arrangements and instrumentalities shown.

DETAILED DESCRIPTION OF THE INVENTION

Figure 1:
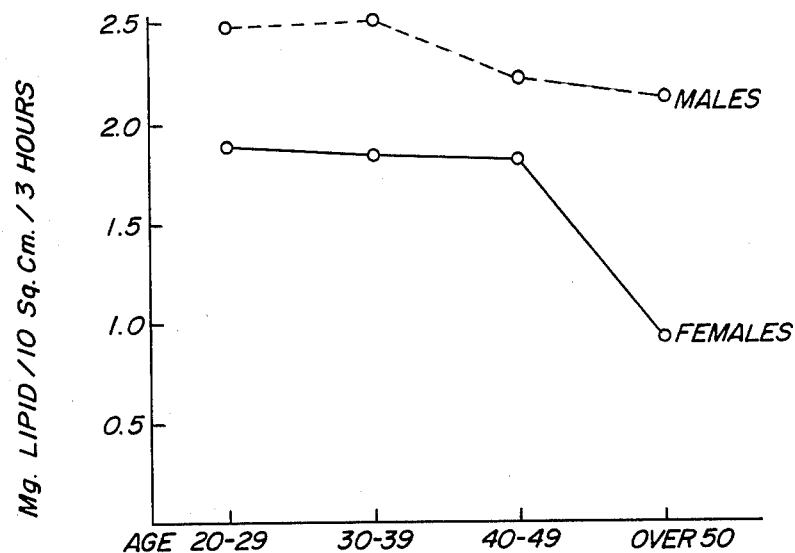
FIG. 1 is a graph demonstrating the reduction in mean sebum (oil) secretion in males and females in relation to advancing age.
Figure 2:
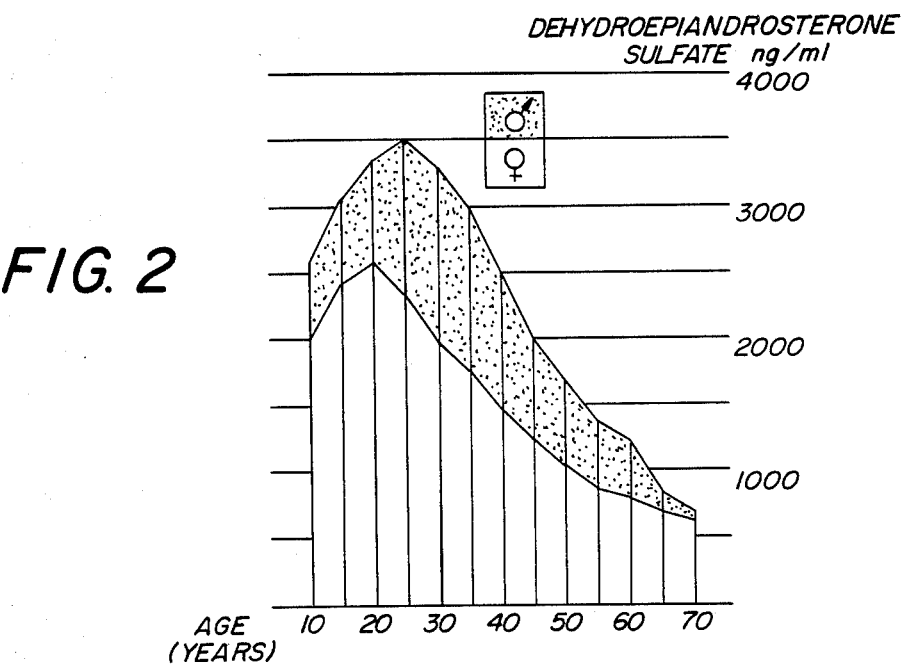
FIG. 2 is a graph of dehydroepiandrosterone sulfate levels in the blood as a function of age.

To permit quantitative evaluation of the effectiveness and degree of localization of the topical application of various amounts of the free alcohol form of dehydroepiandrosterone and its derivatives, e.g., acetate, an animal model, hamsters, was chosen that would permit direct examination and quantitation of the size of sebaceous glands as a function of the treatment according to this invention. The use of a hamster ear for sebaceous gland testing was described by Plewig, G. and Luderschmidt, "Hamster Ear Model for Sebaceous Glands", *Journal of Investigative Dermatology*, 68:171–176 (1977).

Hamster sebaceous glands have been used by numerous medical researchers as an effective and medically accepted animal model for the evaluation of pharmacological products and are directly translatable to their use on human subjects. This model has the advantage of reacting to androgens, estrogens, and other hormones and steroid formulations in a manner closely related to those experienced in the treatment of human beings.

Sebaceous gland cells grow in size as they fill with sebum until they reach full maturity at which point they break open and release their sebum to the surface of the skin. Measurement of sebaceous gland size is thus an effective indicator of the amount of sebum (oil) that is delivered to the surface of the skin. Large glands produce large amounts of sebum, while small glands produce small amounts, thus large glands are associated with oily skin; small glands with dry skin. Hamster ears have sebaceous glands which are readily treatable and easily measured. Accordingly, tests were conducted in which one ear of a hamster was treated with dehydroepiandrosterone (DHEA) and/or a pharmaceutically acceptable, therapeutically effective derivative thereof in a suitable base vehicle while the contralateral ear (the control) was treated with the same base vehicle without the dehydroepiandrosterone (DHEA), and the resultant changes in the gland size of the ear treated with DHEA and the control animal ear were compared.

When the effect of treatment is systemic, both ears will be affected and significant gland size changes will occur on both ears. It is preferred during testing to have a response at the site of application only, e.g., no systemic effect from local application.

The treatment according to this invention was also compared to other known treatments (use of androgens such as testosterone) to produce sebaceous gland enlargement. These other treatments are generally not usable because of their undesirable side effects and systemic action. In the tests used for evaluation, hamsters were treated on one ear with 1% by weight of the free alcohol form of dehydroepiandrosterone in 50 microliters of a suitable vehicle and on the other ear with 50 microliters of the vehicle alone. Similar applications of 1% by weight of various androgens in the same vehicle on other hamsters were used for comparison. A total of 149 hamsters were used to insure statistical validity. Both gel and tincture vehicles were used.

Figure 3:
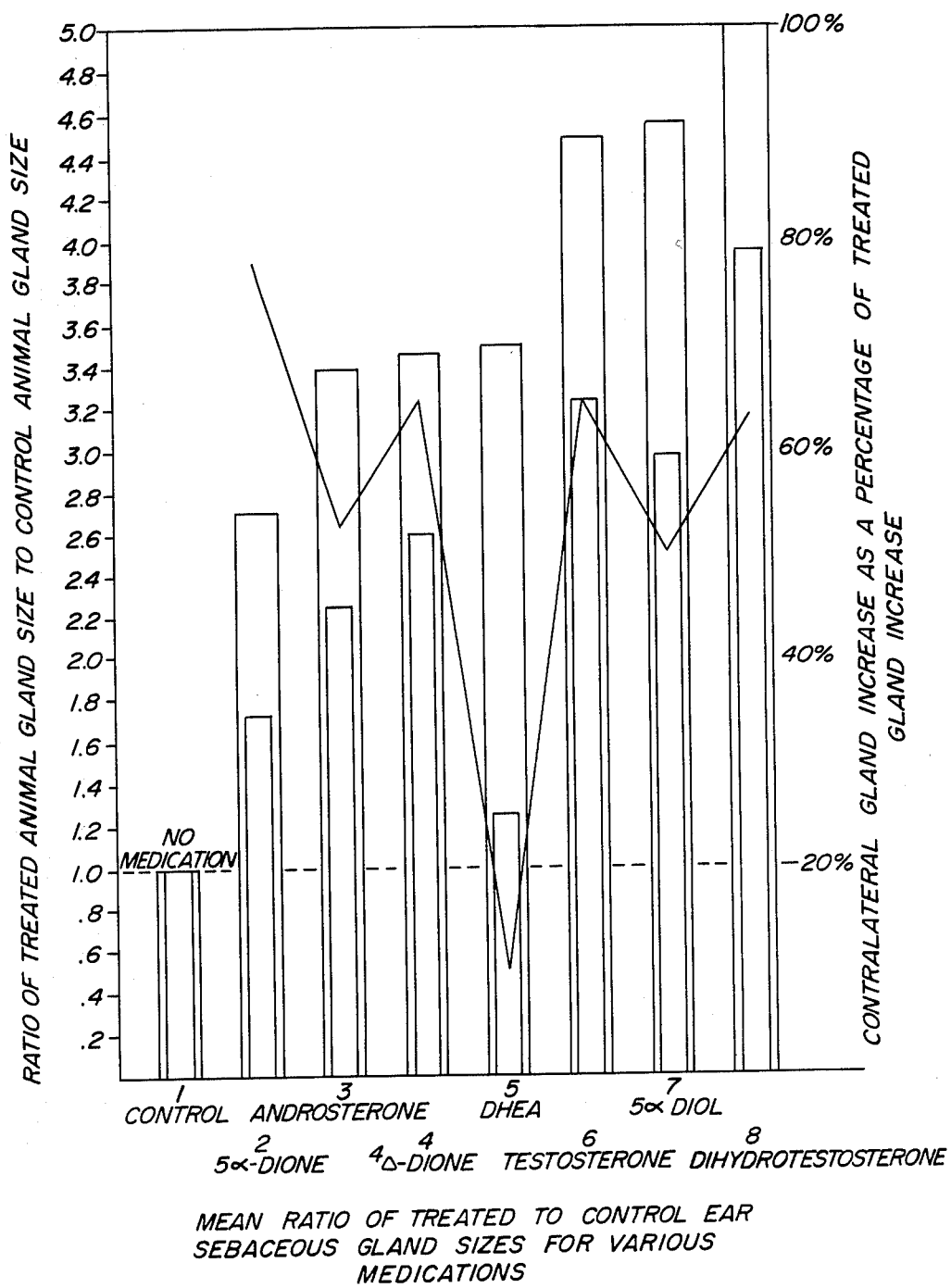
FIG. 3 is a pair of bar plots depicting the change in the size of the sebaceous glands of an animal after treatment according to this invention and with various androgens.

FIG. 3 shows a bar plot of the increase in the size of the sebaceous glands of between about 6 and 10 hamsters per group after treatment with the free alcohol form of dehydroepiandrosterone (DHEA) and with various other androgens. The outer bar in each instance is the ratio of the mean size of sebaceous glands of the treated hamster ear to the mean size of the sebaceous glands of the ears of control hamsters. The inner bar is the ratio of the mean size of sebaceous glands of the untreated contralateral ear of treated hamsters to the mean size of the sebaceous glands of the ears of control hamsters. The scale is on left of the plot.

It can be seen from FIG. 3, that all the androgens tested produced statistically significant systemic effects as measured by the increase of the gland sizes of the contralateral ear (inner bar), while DHEA had no statistically significant systemic effects. In these tests the hamsters were treated once per day for five days a week for two weeks with 50 microliters of a 1% solution (weight/volume) in a tincture vehicle.

FIG. 3 shows the statistically insignificant systemic effect of dehydroepiandrosterone compared to the other androgens tested. The curve interconnecting the points in the center of each bar is a plot of the systemic effect as a percent of contralateral untreated ear sebaceous gland size versus the sebaceous gland size of the treated ear. The percentage scale is on right side of the plot; no systemic effect is at the bottom of the graph corresponding to no increase on the contralateral side and 100% systemic effect is at the top. As is shown, the systemic effect of dehydroepiandrosterone was about 15% (statistically insignificant) whereas all the other androgens tested had systemic effects in excess of 50%.

Figure 4:
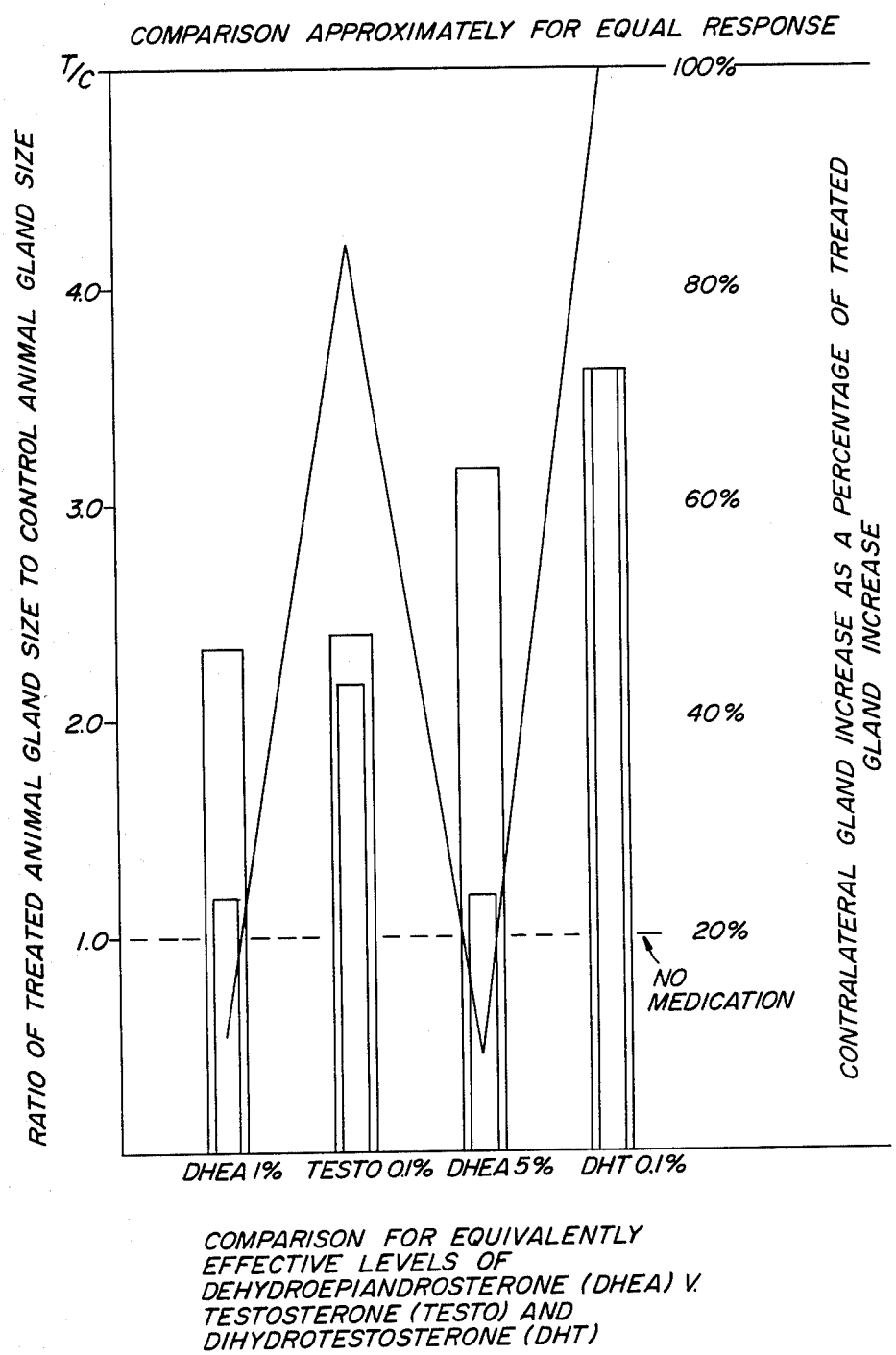
FIG. 4 is a bar graph comparing dehydroepiandrosterone at two different dosages causing equivalent responses as certain doses of testosterone and dihydrotestesterone, respectively.

FIG. 4 shows a bar graph comparing dehydroepiandrosterone ("DHEA") at 1% weight/volume in a tincture vehicle to a dose of testosterone ("testo") (0.1%)

causing an equivalent response and dehydroepiandrosterone at 5% weight/volume to a dose of dihydrotestosterone ("DHT") (0.1%) causing an approximately equivalent response. Treatment was once per day for five days a week for two weeks. All values represent the ratio of the mean size of sebaceous glands of treated hamsters to the mean size of sebaceous glands of control hamsters. The outer and inner bars are defined as set forth above for FIG. 3. The scale is on the left of the plot. Only dehydroepiandrosterone showed unilateral performance. The curve (as in FIG. 3 and with its scale on the right) shows the systemic effect of dehydroepiandrosterone as less than 10% (statistically insignificant), whereas testosterone and dihydrotestosterone have systemic effects of over 80%.

Figure 5:
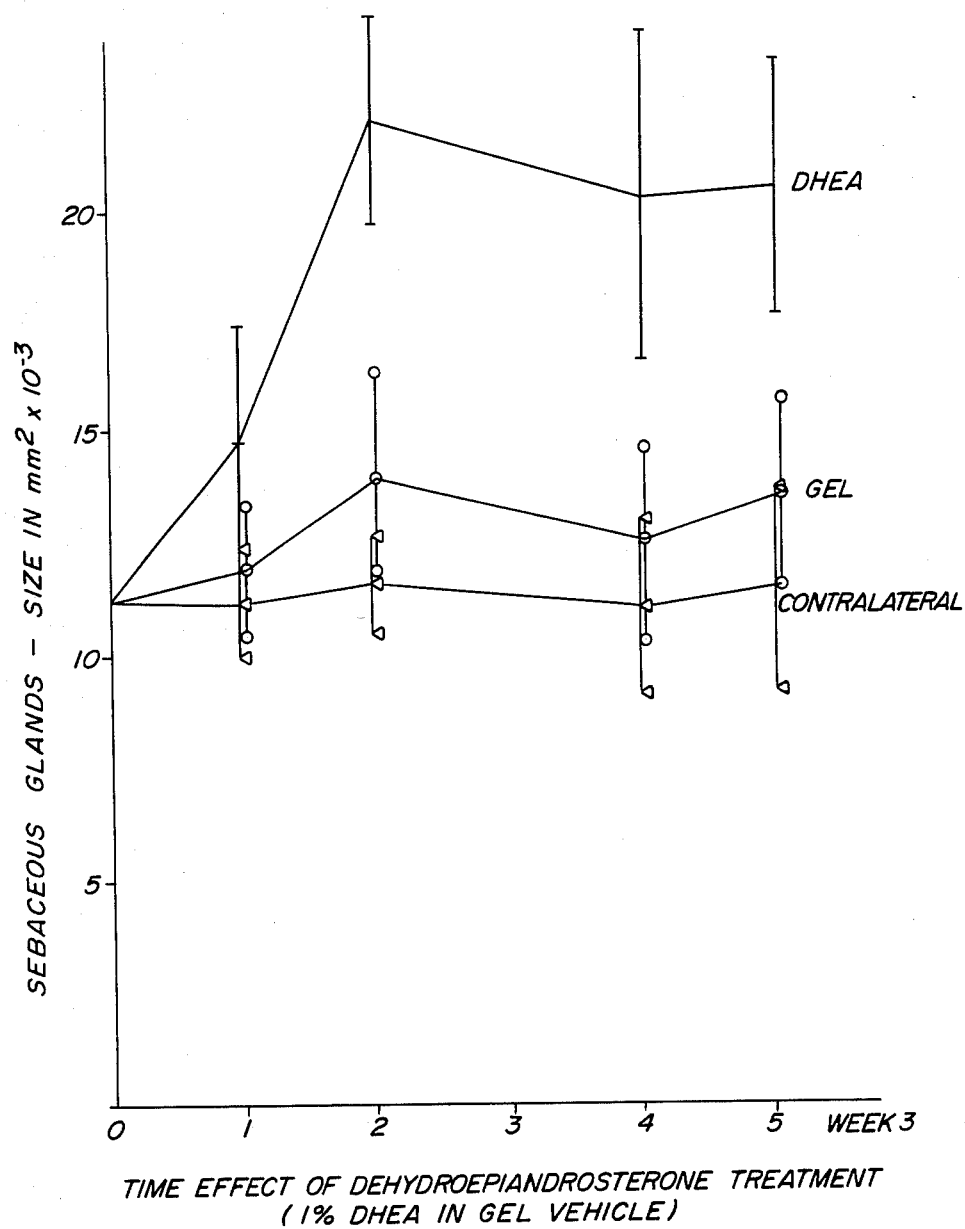
FIG. 5 is a plot of the mean size of the sebaceous gland of the animal ears treated with dehydroepiandrosterone in a gel, untreated ears and control animals treated with the gel without dehydroepiandrosterone, all varying as a function of time.

FIG. 5 shows a plot of the mean size of sebaceous glands of ears treated once per day for five days a week with dehydroepiandrosterone (1% weight/volume) in a gel vehicle (designated as DHEA), untreated contralateral ears of the same hamsters (designated as contralateral), and control hamsters treated with the gel vehicle without any dehydroepiandrosterone (designated as gel), as a function of the time of treatment. The plot shows that two weeks of treatment produced equilibrium and that the effect on the contralateral ears' sebaceous glands was negligible.

The invention will now be described in further detail by reference to the following specific, non-limiting examples.

EXAMPLES 1-4

These examples concern the preparation of a tincture, topical cream, topical ointment and topical gel, respectively, using vehicles previously used in other preparations and reformulated to optimize the efficacy of the DHEA. The formulations for these preparations are given in the Table hereinbelow.

EXAMPLE NO. 1

Butylene glycol and water were mixed and dissolved into alcohol. The resultant vehicle mixture and DHEA were mixed and dissolved. The resultant formulation was a tincture.

EXAMPLE NO. 2

In this example a topical cream was prepared by first mixing and melting squalane, stearyl alcohol NF, cetyl alcohol, polyethylene glycol cetyl ether, mineral oil NF and petrolatum USP, at 70° C. A second mixture was formed by mixing and dissolving methyl paraben NF and propyl paraben NF in water, at 70° C. The second mixture was slowly added to and mixed with the first mixture to form an emulsion. DHEA was dispersed in the resultant emulsion at 50° C. The resultant composition was slowly cooled with mixing until the composition reached room temperature.

EXAMPLE NO. 3

In this example a topical ointment was prepared. As a first step, glyceryl monostearate was mixed and melted in petrolatum USP at 70° C. As a second step, DHEA was mixed and dissolved in butylene glycol at 70° C. The resultant composition of step 2 was slowly added to the resultant composition of step 1, with mixing. This mixture was then cooled to its congealing point with mixing and then cooled to room temperature without mixing.

EXAMPLE NO. 4

In this example a topical gel was prepared. As a first step, hydroxy propyl cellulose was hydrated and dissolved into water. As a second step, DHEA, butylene glycol and PPG-12-Buteth-16 was dissolved in alcohol. Slowly the resultant mixture of step 2 was added into

TABLE

| | Dehydroepiandrosterone (DHEA) Formulations | | | |
|---|---|---|---|---|
| Ingredients | Example No. 1 Topical Tincture % w/w | Example No. 2 Topical Cream/Lotion % w/w | Example No. 3 Topical Ointment % w/w | Example No. 4 Topical Gel % w/w |
| 1. DHEA alcohol acetate valerate, etc any fatty acid ester | 1.0 | 1.0 | 1.0 | 1.0 |
| 2. Methyl Paraben NF | | .01 | | |
| 3. Propyl Paraben NF | | .01 | | |
| 4. Hydroxy Propyl Cellulose (note 1) | | | | 1.0 |
| 5. PPG-12-Buteth-16 (note 2) | | | | 2.0 |
| 6. Squalane (note 3) | | 2.0 | | |
| 7. Glyceryl Monostearate NF | | | 2.0 | |
| 8. Stearyl Alcohol NF | | 2.8 | | |
| 9. Cetyl Alcohol NF | | 4.2 | | |
| 10. Polyethylene Glycol Cetyl Ether (note 4) | | 5.0 | | |
| 11. Mineral Oil NF | | 5.0 | | |
| 12. Butylene Glycol | 4.0 | | 12.0 | 4.0 |
| 13. Petrolatum USP | | 5.4 | 85.0 | |
| 14. Alcohol (note 5) | 89.0 | | | 47.0 |
| 15. Water | 6.0 | 74.4 | | 45.0 |
| | 100.0 | 100.0 | 100.0 | 100.0 |

Notes:
(1) available under the trademark Klucel ® from Hercules
(2) avaialable under the trademark Ucon ® fluid 50HB from Union Carbide
(3) available under the trademark Robane ® from Robeco
(4) available under the trademark Brij 58 ® from ICI
(5) contains 95% ethanol and 5% water the resultant mixture of step 1 with mixing until a gel formed.

The present invention may be embodied in other specific forms without departing from the spirit or essential attributes thereof and, accordingly, reference should be made to the appended claims, rather than to the foregoing specification, as indicating the scope of the invention.

I claim:

1. A method of treating dry skin in a patient which comprises topically administering to the area of dry skin on the patient an effective amount of dehydroepiandrosterone and/or a pharmaceutically acceptable, therapeutically effective derivative thereof.

2. A method of treating dry skin according to claim 1 wherein said derivative is the acetate derivative.

3. A method of treating dry skin according to claim 1 wherein said topical administration is in the form of a tincture.

4. A method of treating dry skin according to claim 1 wherein said topical administration is in the form of a cream.

5. A method of treating dry skin according to claim 1 wherein said topical administration is in the form of a ointment.

6. A method of treating dry skin according to claim 1 wherein said topical administration is in the form of a gel.

* * * * *

UNITED STATES PATENT AND TRADEMARK OFFICE
CERTIFICATE OF CORRECTION

PATENT NO. : 4,496,556

DATED : January 29, 1985

INVENTOR(S) : Norman Orentreich

It is certified that error appears in the above-identified patent and that said Letters Patent is hereby corrected as shown below:

In line 1 of the Abstract, "in" should read -- and --.
In Sheet 4, FIG. 5 of the drawings, in the label of abscissa, "WEEK 3" should read -- WEEKS --. Column 1, line 20 delete "and", so it will read: -- over thirty-five, most women--; Column 1, line 25, "Pochi. P.E." should read: -- Pochi, P.E. --. Column 2, line 29, "dehydroepiandrosterone", should read -- dehydro-epiandrosterone sulfate--. Column 3, line 36, "gland" should read -- glands--; Column 3, line 51 and 52 add -- C., -- so it will read: Luderschmidt, C.,. Column 4, line 31, "insure" should read -- ensure--; Column 4, line 45, delete "," so it will read: -- FIG. 3 that all--.

Signed and Sealed this

Twenty-seventh Day of August 1985

[SEAL]

Attest:

DONALD J. QUIGG

Attesting Officer

Acting Commissioner of Patents and Trademarks